United States Patent
Reydel

(10) Patent No.: US 6,767,339 B2
(45) Date of Patent: Jul. 27, 2004

(54) BODY CANAL INTRUSION INSTRUMENTATION HAVING BIDIRECTIONAL COEFFICIENT OF SURFACE FRICTION WITH BODY TISSUE

(75) Inventor: Boris Reydel, Passaic, NJ (US)

(73) Assignee: Wilson-Cook Medical, Inc., Winston-Salem, NC (US)

( * ) Notice: Subject to any disclaimer, the term of this patent is extended or adjusted under 35 U.S.C. 154(b) by 172 days.

(21) Appl. No.: 10/151,585

(22) Filed: May 16, 2002

(65) Prior Publication Data

US 2003/0018307 A1 Jan. 23, 2003

Related U.S. Application Data

(63) Continuation-in-part of application No. 09/184,331, filed on Nov. 2, 1998, now Pat. No. 6,589,213, which is a continuation-in-part of application No. 08/989,413, filed on Dec. 12, 1997, now abandoned.
(60) Provisional application No. 60/292,146, filed on May 18, 2001.

(51) Int. Cl.$^7$ ................................................. A61M 5/32
(52) U.S. Cl. ........................ 604/175; 604/264; 604/523; 604/910
(58) Field of Search ................................ 604/264, 523, 604/516, 93.01, 94.01, 910, 270, 174, 175, 544, 517, 541, 543; 606/198; 623/1.11, 23.74, 23.64–23.66; 600/129, 139, 585, 433, 435

(56) References Cited

U.S. PATENT DOCUMENTS

| | | |
|---|---|---|
| 3,399,668 A | 9/1968 | Lundgren |
| 3,635,223 A | 1/1972 | Klieman |
| 3,665,928 A | 5/1972 | Del Guercio |
| 3,938,529 A | 2/1976 | Gibbons |
| 4,184,497 A | 1/1980 | Kolff et al. |
| 4,207,872 A | 6/1980 | Meiri et al. |
| 4,465,072 A | 8/1984 | Taheri |
| 4,592,341 A * | 6/1986 | Omagari et al. ............ 600/104 |
| 4,959,057 A | 9/1990 | Lang |
| 5,009,659 A | 4/1991 | Hamlin et al. |
| 5,052,998 A * | 10/1991 | Zimmon ........................ 604/8 |
| 5,059,169 A | 10/1991 | Zilber |
| 5,092,348 A | 3/1992 | Dubrul et al. |
| 5,256,146 A | 10/1993 | Ensminger et al. |
| 5,336,164 A | 8/1994 | Snider et al. |
| 5,395,331 A | 3/1995 | O'Neill et al. |
| 5,454,364 A | 10/1995 | Krüger |
| 5,487,730 A | 1/1996 | Marcadis et al. |
| 5,693,014 A | 12/1997 | Abele et al. |
| 5,762,631 A | 6/1998 | Klein |
| RE35,849 E * | 7/1998 | Soehendra ...................... 604/8 |
| 5,871,475 A * | 2/1999 | Frassica ...................... 604/264 |
| 5,902,285 A | 5/1999 | Kudsk et al. |
| 5,984,896 A | 11/1999 | Boyd |
| 5,989,230 A * | 11/1999 | Frassica ...................... 604/264 |
| 6,004,302 A | 12/1999 | Brierley |
| 6,063,069 A | 5/2000 | Cragg et al. |
| 6,248,100 B1 * | 6/2001 | de Toledo et al. .......... 604/540 |
| 6,293,907 B1 | 9/2001 | Axon et al. |
| 6,293,958 B1 * | 9/2001 | Berry et al. ................. 606/191 |
| 6,482,178 B1 * | 11/2002 | Andrews et al. ........ 604/164.01 |
| 6,558,349 B1 * | 5/2003 | Kirkman ...................... 604/104 |
| 6,663,589 B1 * | 12/2003 | Halevy ...................... 604/96.01 |
| 2001/0041874 A1 * | 11/2001 | Reydel ........................ 604/266 |

FOREIGN PATENT DOCUMENTS

| | | |
|---|---|---|
| WO | WO 97/43941 | 11/1997 |
| WO | WO 98/33469 | 8/1998 |
| WO | WO 99/29362 | 6/1999 |
| WO | WO 00/06239 | 2/2000 |
| WO | WO 00/13736 | 3/2000 |
| WO | WO 00/69498 | 11/2000 |

* cited by examiner

Primary Examiner—Brian L. Casler
Assistant Examiner—Cris L. Rodriguez
(74) Attorney, Agent, or Firm—Brinks Hofer Gilson & Lione

(57) ABSTRACT

A medical device, such as a nasal-jejunal feeding tube, having an arrangement of flaps cut from the outer surface of the catheter and configured so as to not readily adhere to the catheter outer surface. The arrangement of flaps are configured to resist egress so as to permit peristaltic contractions of the body to propel the device forward, yet will allow the device to be removed from the body without the flaps causing significant trauma to the tissues of the body canal.

22 Claims, 1 Drawing Sheet

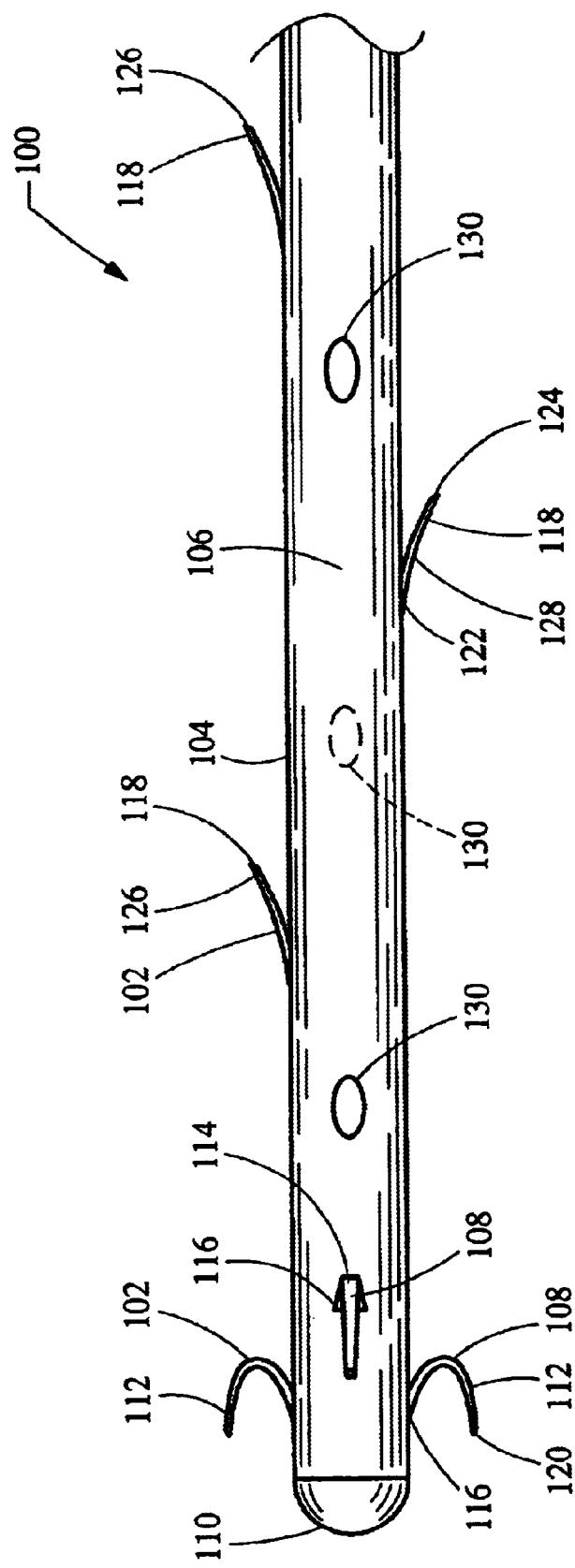

BODY CANAL INTRUSION INSTRUMENTATION HAVING BIDIRECTIONAL COEFFICIENT OF SURFACE FRICTION WITH BODY TISSUE

RELATED APPLICATIONS

This application is continuation-in-part of U.S. application Ser. No. 09/184,331, filed Nov. 2, 1998 now U.S. Pat. No. 6,589,213, which is a continuation-in-part of U.S. application Ser. No. 08/989,413, filed Dec. 12, 1997 (now abandoned), both entitled "Body Canal Intrusion Instrumentation Having Bidirectional Coefficient of Surface Friction with Body Tissue".

This application also claims the benefit of U.S. Provisional Application No. 60/292,146, filed May 18, 2001, entitled "Body Canal Intrusion Instrumentation Having Bidirectional Coefficient of Surface Friction with Body Tissue".

TECHNICAL FIELD OF THE INVENTION

This invention relates to instrumentation for invading body canals non-destructively and with a minimum of trauma, and more particularly, to the interface between the instruments and body tissue during dynamic ingress and egress of surgical instrumentation into the canals.

BACKGROUND OF THE INVENTION

It has been the direction of the prior art to fashion the surface structure of instrumentation used for the non-destructive invasion of body canals with a very slippery surface to facilitate ingress of the instrumentation into the body canal. The resulting slippery surface also produces low friction during egress of the instrumentation from the body canal.

As set forth in detail in U.S. application Ser. No. 09/184, 331, filed Nov. 2, 1998, entitled "Body Canal Intrusion Instrumentation Having Bidirectional Coefficient of Surface Friction with Body Tissue", and which is hereby incorporated by reference, it has been found that the ingress of the medical device or other instrumentation into a desired body site can be facilitated by the utilization of a surface structure on the device having a bi-directional coefficient of friction with respect to the tissue within the body cavity or canal that is engaged by the device during ingress. For example, it has been found that naturally occurring peristaltic contractions tend to grasp and carry the device toward the desired work site. This significantly decreases the risk of puncture by the device, as well as reduces the time required by the surgeon for entry and positioning of the device at the desired work site. These advantages are particularly important during procedures such as the insertion of a gastric or jejungal feeding tube through the esophagus and into or through the stomach or small intestine.

Large flaps or barbs have been used on the outside surface of catheters and related devices for the purpose of stabilizing or anchoring the device within the body canal. These flaps or barbs are designed to prevent both ingress and egress of the device once the device has been positioned at the desired location within the body canal. These flaps or barbs are typically rigid, and are attached to the outside of the device in a hinged manner. However, these devices can be very traumatic to the tissue of the body canal, and can be very uncomfortable to the patient, when manipulated within the body or upon egress from the body canal.

In view of the above, there is a need for a medical device or other instrumentation having a series of flaps that function in a bi-directional manner to engage the tissue of the body canal so as to assist with ingress of the device, but which will permit egress of the device without causing trauma or discomfort to the patient.

BRIEF SUMMARY OF THE INVENTION

The foregoing problems are solved and a technical advance is achieved in a medical device, such as a gastrointestinal catheter, for use in delivering fluid-like materials to the gastrointestinal tract. Such fluid-like materials could include feeding materials, drugs, contrast materials or saline.

The illustrative embodiment of the present invention is directed to a nasal-jejunal feeding tube having an arrangement of flaps cut from the outer surface of the catheter and configured so as to not readily adhere to the catheter outer surface. The arrangement of flaps are also configured so as to resist egress to the degree that allows the body to propel the device forward, yet will allow the device to be removed from the body without the flaps causing significant trauma, such as inflammation, to the tissues of the body canal, and thereby minimizing or eliminating patient discomfort.

The preferred embodiment illustrated herein comprises a 14 FR nasal-jejunal feeding tube having a minimum overall length of 154 cm. A series of flaps are formed on the outer surface of the distal 50 cm of the catheter portion. Four longer flaps are formed near the distal end of the feeding tube, and are arranged about the perimeter of the feeding tube at approximately equal intervals (i.e., at 90° intervals with respect to each other). A number of shorter flaps are distributed along the length of the feeding tube inwardly or proximally from the four longer flaps. These shorter flaps alternate along opposite sides of the feeding tube at approximately 2 cm intervals for the distal 50 cm of the catheter. The feeding tube also includes several apertures distributed along the distal portion of the catheter. These feeding tube apertures alternate along opposite sides of the feeding tube at approximately 2 cm intervals, and are generally disposed at 900 intervals with respect to the shorter flaps.

BRIEF DESCRIPTION OF THE DRAWING

FIG. 1 is a side view of an illustrative embodiment of a body canal intrusion instrument in accordance with the teachings of this invention. In particular, FIG. 1 is a side view of the distal portion of a nasal-jejunal feeding tube made in accordance with the teachings of this invention.

DETAILED DESCRIPTION OF THE INVENTION

The present invention is directed to a medical device 100, such as a gastrointestinal catheter, for use in delivering fluid-like materials to the gastrointestinal tract. Such fluid-like materials could include feeding materials, drugs, contrast materials or saline. In particular, an illustrative embodiment of the present invention is shown in FIG. 1, which depicts the distal portion of a nasal-jejunal feeding tube having a plurality of bidirectional surface elements 102 distributed along the outer surface 104 of the catheter portion 106 of the device 100.

In the illustrative embodiment shown, a group of four (4) distal flaps 108 are disposed about the perimeter of the catheter outer surface 104 at approximately equal intervals (i.e., at 90° intervals). The distal flaps 108 are positioned near the distal tip 110 of the device 100. In the preferred embodiment, the distal flaps 108 comprise a first oppositely disposed pair of distal flaps 112 located approximately 0.7 cm from the distal tip 110 of the feeding tube 100, and a second oppositely disposed pair of distal flaps 114 located approximately 1.0 cm from the distal tip 110 of the device 100, as measured from the base 116 of each of the flaps 112, 114.

In the preferred embodiment shown, each of the distal flaps 108 are approximately 1.0 cm in length, when straightened. The distal flaps 108 are preferably formed by cutting a portion of the catheter outer surface 104. In addition, each of the distal flaps 108 are curved (or curled) so as to prevent the flaps 108 from adhering to the outer surface 104 of the catheter, and so as to orient the tips 120 of the distal flaps 108 forwardly (i.e., towards the distal tip 110 of the device 100). Preferably, each of the distal flaps 108 is curved by utilizing a cutting technique that results in the formation of a distal flap 108 that tends to curve outwardly from the outer surface 104 of the catheter. Depending on the type of material from which the catheter is manufactured, curving of the distal flaps 108 may also be accomplished by heat curving.

The configuration and orientation of the distal flaps 108 resist egress of the device 100, and also causes the device to be propelled forwardly by naturally occurring peristaltic contractions of the tissue of the body canal (not shown). In particular, when the device 100 is being inserted into the body canal, the distal flaps 108 provide a relatively large diameter near the distal tip 110 of the device 100 that can be readily grasped by the tissue of the body canal during peristaltic contractions. However, when the device 100 is being removed from the body canal, the forward orientation of the tips 120 prevent trauma to the tissue. In addition, the distal flaps 108 are sufficiently flexible to prevent trauma to the tissue of the body canal upon either ingress or egress of the device 100.

A plurality of secondary flaps 118 are disposed along the outer surface 104 of the catheter inwardly (or proximal) from the distal tip 110 and the distal flaps 108. In the preferred embodiment shown, the secondary flaps 118 are distributed along the distal 50 cm of the catheter portion 106 of the feeding tube. The secondary flaps 118 alternate along opposite sides of the feeding tube at approximately 2 cm intervals. In other words, the secondary flaps 118 comprise a first series of secondary flaps 126 disposed along the top side of the feeding tube (as viewed in FIG. 1) and spaced at approximately 4 cm intervals, and a second series of secondary flaps 128 disposed along the bottom side of the feeding tube (as viewed in FIG. 1) and spaced there between.

Although not shown in the drawing of the illustrative embodiment, it should be appreciated that the secondary flaps 118 can be arranged in numerous other configurations. For example, the secondary flaps 118 can be disposed along the catheter portion 106 of the feeding tube in a spiral or random configuration. The secondary flaps 118 can also be disposed along more than two sides of the catheter portion 106. It is also not necessary for the secondary flaps 118 to be disposed in an alternating fashion along opposite sides of the catheter portion 106.

In the preferred embodiment, each of the secondary flaps 118 measures approximately 0.5 cm in length, when straightened. Each of the secondary flaps 118 has a truncate shape comprising a base 122 measuring approximately 0.016 cm in width, and a tip 124 measuring approximately 0.010 cm in width. The secondary flaps 118 are preferably formed by cutting a portion of the catheter outer surface 104.

In addition, each of the secondary flaps 118 are moderately curved outwardly so as to prevent the secondary flaps 118 from adhering to the outer surface 104 of the catheter, and to allow the tip 124 to engage the tissue of the body canal (not shown). Preferably, each of the secondary flaps 118 is curved by utilizing a cutting technique that results in the formation of a secondary flap 118 that tends to curve outwardly from the outer surface 104 of the catheter. Depending on the type of material from which the catheter is manufactured, curving of the secondary flaps 118 may also be accomplished by heat curving.

The secondary flaps 118 are also configured so as to orient the tips 124 of the secondary flaps 118 rearwardly (ie., away from the distal tip 110 of the device 100). This rearward orientation of the secondary flaps 118 resist egress of the device 100, and causes the device to be propelled forwardly by naturally occurring peristaltic contractions of the tissue of the body canal during the insertion process. In addition, the relatively low profile of the secondary flaps 118 minimizes trauma to the tissue during the removal process. The secondary flaps 118 are also sufficiently flexible to prevent trauma to the tissue of the body canal upon either ingress or egress of the device 100.

The feeding tube further comprises feeding tube apertures 130 disposed along the distal portion of the catheter. The feeding tube apertures measure approximately 0.5 cm in diameter, and provide openings through which feeding material can exit the interior of the feeding tube and enter the body canal or cavity. In the embodiment shown, the feeding tube apertures 130 are alternately disposed along opposite sides of the feeding tube at approximately 2 cm intervals, and are preferably located on the sides of the feeding tube that are 90° offset from the sides of the feeding tube along which the secondary flaps 118 are located (i.e., along the front and back sides of the feeding tube as viewed in FIG. 1). The illustrative embodiment comprises a total of five (5) feeding tube apertures 130.

The above described arrangement and dimensions provided for elements thereof are merely exemplary. Any other undisclosed or incidental details of the construction or composition of the various elements of the disclosed embodiments of the present invention are not considered to be critical to the achievement of the advantages of the present invention, so long as the elements possess the attributes required to perform as disclosed herein. The selection of these and other details of construction are believed to be well within the ability of one of ordinary skill in the relevant art in view of the present disclosure. Illustrative embodiments of the present invention have been described in detail for the purpose of disclosing practical, operative structures whereby the invention may be practiced advantageously. The designs described herein are intended to be exemplary only. The novel characteristics of the invention may be incorporated in other structural forms without departing from the spirit and scope of the invention.

What is claimed is:

1. A medical device controllable from outside a subject's body for dynamic movement into a body canal toward an interior body work site and removal therefrom, the device comprising an elongate member having a plurality of distal flaps disposed on a surface of the elongate member near a distal tip thereof, said distal flaps projecting outwardly from the surface of the elongate member a distance sufficient to engage an interior surface of the body canal during peristaltic contractions, said distal flaps being configured so as to promote ingress of said device in response to said peristaltic contractions, said distal flaps being sufficiently flexible to minimize trauma to the interior surface of the body canal during egress of the device, said device further comprising a plurality of secondary flaps disposed on the surface of the elongate member, said secondary flaps having a shape and size that is different from said distal flaps, said secondary flaps being configured so as to promote ingress of said device in response to said peristaltic contractions, and being sufficiently flexible to minimize trauma to the interior surface of the body canal during egress of the device.

2. The medical device according to claim 1 wherein said distal flaps and said secondary flaps comprise tips that are generally oriented in opposite directions.

3. The medical device according to claim 2 wherein said distal flaps and said secondary flaps are formed from a portion of the surface of said elongate member.

4. The medical device according to claim 3 wherein said distal flaps and said secondary flaps are configured so as to extend outwardly from the surface of said elongate member.

5. The medical device according to claim 4 wherein said distal flaps and said secondary flaps are configured to extend outwardly from the surface of said elongate member by a heat treatment process.

6. The medical device according to claim 1 wherein said distal flaps each comprise a length that is at least twice as long as a length of each of said secondary flaps.

7. The medical device according to claim 1 wherein said distal flaps each extend outwardly from the surface of said elongate member a distance that is at least twice as great as a distance each of said secondary flaps extends outwardly from the surface of said elongate member.

8. The medical device according to claim 1 wherein the plurality of distal flaps are disposed at equal intervals about an outer circumference of the elongate member.

9. The medical device according to claim 8 wherein the plurality of secondary flaps are alternatively disposed along opposite sides of the elongate member.

10. The medical device according to claim 9 further comprising apertures in the surface of the elongate member.

11. The medical device according to claim 1 wherein said elongate member comprises a hollow catheter.

12. The medical device according to claim 1 wherein said elongate member comprises a nasal-jejunal feeding tube.

13. A gastrointestinal catheter for insertion into a patient and controllable from outside the patient's body, said gastrointestinal catheter configured for dynamic movement into and through the patient's gastrointestinal tract, the feeding tube comprising:

a hollow catheter having a distal tip and an outer surface;

a plurality of distal flaps disposed on a surface of the catheter, said distal flaps being circumferentially disposed about the outer surface of the catheter near a distal tip thereof, said distal flaps projecting outwardly from the surface of the catheter so as to engage an interior surface of the gastrointestinal tract and configured so as to promote ingress of the feeding tube in response to peristaltic contractions, said distal flaps being sufficiently flexible to minimize trauma to the interior surface of the gastrointestinal tract during egress of the feeding tube;

a plurality of secondary flaps disposed on the outer surface of the catheter, said secondary flaps having a shape, size and orientation that is different from said distal flaps, said secondary flaps being configured so as to promote ingress of the feeding tube in response to said peristaltic contractions, said secondary flaps being sufficiently flexible to minimize trauma to the interior surface of the gastrointestinal tract during egress of the feeding tube; and a plurality of apertures disposed along the catheter, said apertures configured to permit fluid-like materials within the catheter to enter the gastrointestinal tract.

14. The gastrointestinal catheter according to claim 13 wherein said distal flaps each comprise a hook-shape and having a tip that is generally oriented towards the distal tip of the catheter.

15. The gastrointestinal catheter according to claim 13 wherein said distal flaps each comprise a tip that is generally oriented towards the distal tip of the catheter, and said secondary flaps each comprise a tip that is generally oriented in away from the distal tip of the catheter.

16. The gastrointestinal catheter according to claim 13 wherein said distal flaps and said secondary flaps are each formed from a portion of the outer surface of said catheter.

17. The gastrointestinal catheter according to claim 13 wherein said distal flaps and said secondary flaps are each biased to extend outwardly from the outer surface of said catheter by a heat treatment process.

18. The gastrointestinal catheter according to claim 13 wherein said distal flaps each comprise a length that is at least twice as long as a length of each of said secondary flaps.

19. The gastrointestinal catheter according to claim 13 wherein said distal flaps each extend outwardly from the outer surface of said catheter a distance that is at least twice as great as a distance each of said secondary flaps extends outwardly from the outer surface of said catheter.

20. The gastrointestinal catheter according to claim 13 wherein the plurality of secondary flaps are alternatively disposed along opposite sides of the catheter.

21. The gastrointestinal catheter according to claim 13 wherein the plurality of apertures are alternatively disposed along opposite sides of the catheter.

22. The gastrointestinal catheter according to claim 13 wherein the plurality of distal flaps comprises four distal flaps disposed at 90° intervals about the outer surface of the catheter, wherein the plurality of secondary flaps are alternatively disposed at equal intervals along a first pair of opposite sides of the catheter, and wherein the plurality of apertures are alternatively disposed at equal intervals along a second pair of opposite sides of the catheter.

* * * * *